United States Patent
Hwu et al.

(10) Patent No.: US 11,371,924 B2
(45) Date of Patent: Jun. 28, 2022

(54) METHOD FOR IMAGING COMPOUND CONTAINED BY LIPID VESICLE IN WATER AND EXAMINING METHOD FOR THE SAME

(71) Applicant: Yeu-Kuang Hwu, New Taipei (TW)

(72) Inventors: Yeu-Kuang Hwu, New Taipei (TW); Yu-Fang Hu, Taipei (TW); Shun-Min Yang, Taipei (TW); Chi-Feng Huang, Taoyuan (TW)

(73) Assignee: Yeu-Kuang Hwu, New Taipei (TW)

( * ) Notice: Subject to any disclaimer, the term of this patent is extended or adjusted under 35 U.S.C. 154(b) by 236 days.

(21) Appl. No.: 16/729,052

(22) Filed: Dec. 27, 2019

(65) Prior Publication Data

US 2020/0209131 A1    Jul. 2, 2020

(30) Foreign Application Priority Data

Dec. 28, 2018 (TW) ............................ 107147775

(51) Int. Cl.
*G06K 9/00* (2022.01)
*G01N 15/02* (2006.01)
(Continued)

(52) U.S. Cl.
CPC .......... *G01N 15/0211* (2013.01); *A61K 9/127* (2013.01); *G06T 7/0012* (2013.01);
(Continued)

(58) Field of Classification Search
None
See application file for complete search history.

(56) References Cited

U.S. PATENT DOCUMENTS

2013/0101664 A1* 4/2013 Kufe ...................... A61K 45/06
424/450
2018/0169009 A1* 6/2018 Johnson ............... A61K 47/543
(Continued)

OTHER PUBLICATIONS

Chapman: "Structure Determination Using X-Ray Free-Electron Laser Pulses" Protein Crystallography: Methods and Protocols, Methods in Molecular Biology, vol. 1607, 2017, pp. 295-324. (Year: 2017).*

(Continued)

*Primary Examiner* — Wei Wen Yang
(74) *Attorney, Agent, or Firm* — Muncy, Geissler, Olds & Lowe, P.C.

(57) ABSTRACT

The present disclosure provides a method for imaging a compound contained by a lipid vesicle in water. The method comprises the following steps of: (a) providing an aqueous sample comprising the lipid vesicle which contains the compound, wherein the aqueous sample further comprises ammonium sulphate (($NH_4$)$_2SO_4$); (b) illuminating the aqueous sample with an X-ray free-electron laser (X-FEL); (c) with an image sensor, collecting a plurality of coherent diffraction image patterns of the aqueous sample being illuminated; and (d) reconstructing the coherent diffraction image patterns with a computer such that an image of the lipid vesicle containing the compound is acquired. A method for examining a quality of a chemical drug contained by a liposome in water is also provided.

19 Claims, 7 Drawing Sheets

(51) Int. Cl.
    A61K 9/127    (2006.01)
    G06T 7/00     (2017.01)
    A61K 31/704   (2006.01)
    H01S 3/09     (2006.01)
(52) U.S. Cl.
    CPC ... A61K 31/704 (2013.01); G06T 2207/10116 (2013.01); H01S 3/0903 (2013.01)

(56) References Cited

U.S. PATENT DOCUMENTS

2019/0035616 A1* 1/2019 Longchamp .......... H01J 49/165
2019/0302010 A1* 10/2019 Porter .................... G01N 21/45

OTHER PUBLICATIONS

Cherukara: "Real-time coherent diffraction inversion using deep generative networks." SCieNtifiC RePorts (2018), pp. 1-8. (Year: 2018).*

D. Pile, "First light from SACLA" Nature Photon., 2011, 5, 456-457.

P. Emma, R. Akre, J. Arthur, R. Bionta, C. Bostedt, J. Bozek, A. Brachmann, P. Bucksbaum, R. Coffee and F.-J. Decker, "First lasing and operation of an angstrom-wavelength free-electron laser" Nature Photon., 2010, 4, 641-647.

H. Tanaka et al., "A compact X-ray free-electron laser emitting in the sub angstrom region" Nature Photon., 2012, 6, 540-544.

T. Kimura, Y. Joti, A. Shibuya, C. Song, S. Kim, K. Tono, M. Yabashi, M. Tamakoshi, T. Moriya and T. Oshima, "Imaging live cell in micro-liquid enclosure by X-ray laser diffraction" Nat. Commun., 2014, 5, 3052., pp. 1-7.

M. Gallagher-Jones, Y. Bessho, S. Kim, J. Park, S. Kim, D. Nam, C. Kim, Y. Kim, O. Miyashita and F. Tama, "Macromolecular structures probed by combining single-shot free-electron laser diffraction with synchrontron coherent X-ray imaging" Nat. Commun., 2014, 5, 3798, pp. 1-9.

G. van der Schot, M. Svenda, F. R. Maia, M. Hantke, D. P. DePonte, M. M. Seibert, A. Aquila, J. Schulz, R. Kirian and M. Liang, "Imaging single cells in a beam of live cyanobacteria with an X-ray laser" Nat. Commun., 2015, 6, 5704 pp. 1-9.

T. Ekeberg, M. Svenda, C. Abergel, F. R. Maia, V. Seltzer, J.-M. Claverie, M. Hantke, O. Jonsson, C. Nettelblad and G. van der Schot, "Three-Dimensional Reconstruction of the Giant Mimivirus Particle with an X-Ray Free-Electron Laser" Phys. Rev. Lett., 2015, 114, 098102., pp. 1-6.

M. Watari, R. McKendry, M. Voegtli, G. Aeppli, Y. Soh, X. Shi, G. Xiong, X. Huang, R. Harder, I. K. Robinson, "Differential stress induced by thiol adsorption on facetted nonocrystals" Nat. Mater. 2011, 10, pp. 862-866.

D. Nam, J. Park, M. Gallagher-Jones, S. Kim, S. Kim, Y. Kohmura, H. Naitow, N. Kunishima, T. Yoshida, T. Ishikawa T and C. Song, "Imaging Fully Hydrated Whole Cells by Coherent X-Ray Diffraction Microscopy" Phys. Rev. Lett., 2013, 110, 098103, pp. 1-5.

D. Papahadjopoulos, T. Allen, A. Gabizon, E. Mayhew, K. Matthay, S. Huang, K. Lee, M. Woodie, D. Lasic and C. Redemann, "Sterically stabilized liposomes: Improvements in pharmacokinetics and antitumor therapeutic efficacy" Proc. Natl. Acad. Sci. USA, 1991, 88, 11460-11464.

A. Gabizon, R. Catane, B. Uziely, B. Kaufman, T. Safra, R. Cohen, F. Martin, A. Huang and Y. Barenholz, "Prolonged Ciruclation Time and Enhanced Accumulation in Malignant Exudates of Doxorubicin Encapsulated in Polyethylene-glycol Coated Liposomes" Cancer Res., 1994, 54, 987-992.

D. W. Northfelt, F. J. Martin, P. Working, P. A. Volberding, J. Russell, M. Newman, M. A. Amantea and L. D. Kaplan, "Doxorubicin Encapsulated in Liposomes Containing Surface-Bound Polyethylene Glycol: Pharmacokinetics, Tumor Localization, and Safety in Patients with AIDS-Related Kaposi's Sarcoma" J. Clin. Pharmacol., 1996, 36, 55-63.

J. R. Fienup, "Phase retrieval algorithms: a comparison" Appl. Opt., 1982, vol. 21, No. 15, pp. 2758-2769.

V. Elser, "Phase retrieval by iterated projections" J. Opt. Soc. Am., 2003, vol. 20, No. 1, pp. 40-55.

H. H. Bauschke, P. L. Combettes and D. R. Luke, "Phase retrieval, error reduction algorithm, and Fienup variants: a view from convex optimization" J. Opt. Soc. Am., 2002, vol. 19, No. 7, pp. 1334-1345.

C. Chen, J. Miao, C. Wang and T. Lee, "Application of optimization technique to noncrystalline x-ray diffraction microscopy: Guided hybrid input-output method" Phys. Rev. B, 2007, 76, 064113, pp. 1-5.

T. M. Allen and P. R. Cullis, "Drug Delivery Systems: Entering the Mainstream" Science, 2004, 303, 1818-1822.

A. Samad, Y. Sultana and M. Aqil, "Liposomal Drug Delivery Systems: An Update Review" Curr. Drug. Deliv., 2007, 4, 297-305.

B. C. Keller, "Liposomes in nutrition" Trends Food Sci. Tech., 2001, 12, 25-31.

F. Arcamone, G. Cassinelli, G. Fantini, A. Grein, P. Orezzi, C. Pol and C. Spalla, "Adriamycin, 14-Hydroxydaunomycin, a New Antitumor Antibiotic from *S. peucetius* var. caesius" Biotechnol. Bioeng., 1969, 11, 1101-1110.

R. I. Pakunlu, Y. Wang, M. Saad, J. J. Khandare, V. Starovoytov and T. Minko, J. "In vitro and in vivo intracellular liposomal delivery of antisense oligonucleotides and anticancer drug" Journal of Control. Release, 2006, 114, 153-162.

T. Kubo, T. Sugita, S. Shimose, Y. Nitta, Y. Ikuta and T. Murakami, "Targeted delivery of anticancer drugs with intravenously administered magnetic liposomes in osteosarcoma-bearing hamsters" Int. J. Oncol., 2000, 17, 309-324.

A. A. Gabizon, "Pegylated Liposomal Doxorubicin: Metamorphosis of an Old Drug into a New Form of Chemotherapy" Cancer Invest., 2001, 19 (4), 424-436.

B. Uziely, S. Jeffers, R. Isacson, K. Kutsch, D. Wei-Tsao, Z. Yehoshua, E. Libson, F. M. Muggia and A. Gabizon, "Liposomal Doxorubicin: Antitumor Activity and Unique Toxicities During Two Complementary Phase I Studies" J. Clin. Oncol., 1995, vol. 13, No. 7, 1777-1785.

S. A. Abraham, D. N. Waterhouse, L. D. Mayer, P. R. Cullis, T. D. Madden and M. B. Bally, "The Liposomal Formulation of Doxorubicin" Methods Enzymol, 2005, 391, 71-97.

S. K. Hobbs, W. L. Monsky, F. Yuan, W. G. Roberts, L. Griffith, V. P. Torchilin and R. K. Jain, "Regulation of transport pathways in tumor vessels: Role of tumor type and microenvironment" Proc. Natl. Acad. Sci. USA, 1998, 95, 4607-4612.

Y.-M. Wu, C.-H. Wang, J.-w. Chang, Y.-y. Chen, N. Miyazaki, K. Murata, K. Nagayama and W.-H. Chang, "Zernike phase contrast cryo-electron microscopy reveals 100 kDa component in a protein complex" J. Phys. D Applied Physics, , 2013, 46, 494008., pp. 1-11.

Y.-M. Wu, J.-W. Chang, C.-H. Wang, K. Nagayama, N. Miyazaki, K. Murata and W.-H. Chang, "Zernike Cryo-EM with a Direct Electron Camera Enables Tracking Protein Conformations in the Temporal Dimension" Microsc. Microanal., 2015, 21 (suppl. 3), 2145-2146.

M. Almgren, K. Edwards and G. Karlsson, "Cryo transmission electron microscopy of liposomes and related structures" Colloids Surf. A Physicochemical and Engineering Aspects, 2000, 174, 3-21.

I. V. Zhigaltsev, N. Maurer, Q.-F. Akhong, R. Leone, E. Leng, J. Wang, S. C. Semple and P. R. Cullis, "Liposome-encapsulated vincristine, vinblastine and vinorelbine: A comparative study of drug loading and retention" J. Control. Release, 2005, 104, 103-111.

N. Weiner, F. Martin and M. Riaz, Drug. "Liposomes as a drug delivery system" Dev. Ind. Pharm., 1989, I5 (10), 1523-1554.

M. Kotlarchyk and S. H. Chen, "Analysis of small angle neutron scattering spectra from polydisperse interacting colloids" J. Chem. Phys., 1983, 79, 2461-2469.

C. Song, K. Tono, J. Park, T. Ebisu, S. Kim, H. Shimada, S. Kim, M. Gallagher-Jones, D. Nam, T. Sato, T. Togashi, K. Ogawa, Y. Joti, T. Kameshima, S. Ono, T. Hatsui, S. Iwata, M. Yabashi and T. Ishikawa, "Multiple application X-ray imaging chamber for single-shot diffraction experiments with femtosecond X-ray laser pulses" J. Appl. Cryst., 2014, 47, 188-197.

Y. Takahashi, A. Suzuki, N. Zettsu, T. Oroguchi, Y. Takayama, Y. Sekiguchi, A. Kobayashi, M. Yamamoto and M. Nakasako, Nano

(56) References Cited

OTHER PUBLICATIONS

Lett., "Coherent Diffraction Imaging Analysis of Shape-Controlled Nanoparticles with Focused Hard X-ray Free-Electron Laser Pulses" 2013, 13, 6028-6032.
M. J. Bogan, D. Starodub, C. Y. Hampton and R. G. Sierra, "Single-particle coherent diffractive imaging with a soft x-ray free electron laser: towards soot aerosol morphology" J. Phys. B, At. Mol. Opt. Phys., 2010, 43, 194013, pp. 1-14.
M. Yabashi, T. Ishikawa, "XFEL/SPring-8 Beamline Technical Design Report ver. 2.0" p. 42-46 (Experimental facility group, SPring-8 joint project for XFEL, Hyogo, 2010).
Huang et al., "Nanoscale: Free-electron-laser coherent diffraction images of individual drug-carrying liposome particles in solution", NANOSCALE, 2018, pp. 1-5.
Schilt et al., "Using solution X-ray scattering to determine the high-resolution structure and morphology of PEGylated liposomal doxorubicin nanodrugs" Biochimica et Biophysica Acta, 1860, 2016, pp. 108-119.

* cited by examiner

METHOD FOR IMAGING COMPOUND CONTAINED BY LIPID VESICLE IN WATER AND EXAMINING METHOD FOR THE SAME

CROSS REFERENCE TO RELATED APPLICATIONS

This Non-provisional application claims priority under 35 U.S.C. § 119(a) on Patent Application No. 107147775 filed in Republic of China on Dec. 28, 2018, the entire contents of which are hereby incorporated by reference.

BACKGROUND

Technical Field

The present invention relates to an imaging method, especially relating to the imaging method using free-electron-laser coherent diffraction.

Related Arts

The first X-FELs[1-3] are revolutionizing structural investigations at the submicron level,[4-7] yielding detailed information on individual particles. This was notably demonstrated for metal nanoparticles and viruses of relatively large size.[7-8]

Liposomes are vesicles composed of lipids, used to deliver nutrients or drugs.[17-19] Their excellent, size-dependent delivery properties are specifically employed for carrying doxorubicin, a widely used anticancer drug.[17,20-24] Further improvements, specifically those concerning the size and the homogeneity,[25,26] would be highly desirable for medical and other health related applications, not to mention compliance with the drug-certification requirements. However, these improvements necessitate a detailed knowledge of the structural properties of liposomes that is hard to achieve. It is indeed difficult to identify the shape, size and drug uptake of liposomes by standard imaging methods, particularly in a natural liquid environment, which is an essential condition for a realistic impact on the optimization of drug delivery.

However, cryo-EM cannot be implemented in the natural liquid environment. Conventional SAXS on liquid solutions cannot be applied to anisotropic nanorods with non-uniform size distribution, as in the present case. These are limitations of general significance, since the typical structure of drug-carrying nanoparticles is indeed anisotropic and not uniform. Similar limitations also affect other imaging techniques: for example, dynamic light scattenng[31] provides useful information, but performs averages over many particles and cannot detect the drug rods inside them.

SUMMARY

The approach provided by this disclosure offers marked advantages. In this disclosure, it has been shown that the X-FELs enables the imaging of individual liposome particles with about 100 nm size and in water[9], even though they consist in principle of weakly-scattering biomolecules, and of their carried drugs.[10-12] The diffracted intensity was specifically sufficient for CDI reconstruction[13-16] yielding quantitative information on individual liposome. Moreover, the quantitative X-FEL CDI results provided by this disclosure were generally consistent with cryo-electron microscopy (cryo-EM) data[27-30] and with a small-angle x-ray scattering (SAXS) analysis of the diffraction patterns. This work solved aforementioned issues by using CDI of individual nanoparticles in solution, based on X-FEL pulses. The experiments were performed with a specially designed sample holder to analyze liposomes To achieve the above objective, one embodiment of the invention discloses a method for imaging a compound contained by a lipid vesicle in water. The method comprises the following steps of: (a) providing an aqueous sample comprising the lipid vesicle which contains the compound, wherein the aqueous sample further comprises ammonium sulphate (($NH_4$)$_2SO_4$); (b) illuminating the aqueous sample with an X-ray free-electron laser (X-FEL); (c) with an image sensor, collecting a plurality of coherent diffraction image patterns of the aqueous sample being illuminated; and (d) reconstructing the coherent diffraction image patterns with a computer such that an image of the lipid vesicle containing the compound is acquired.

In one embodiment, the concentration of the ammonium sulphate in the aqueous sample ranges from 1M to 6M.

In one embodiment, the lipid vesicle is a liposome or a micelle.

In one embodiment, the liposome has a size ranging from 70 nm to 250 nm.

In one embodiment, the concentration of the liposome in the aqueous sample ranges from 0.5 liposome/$\mu m^3$ to 1 liposome/$\mu m^3$.

In one embodiment, the X-ray free-electron laser (X-FEL) is 3.9613 keV photon pulses.

In one embodiment, the X-ray free-electron laser (X-FEL) is 425.4 µJ/pulse on an average.

In one embodiment, the aqueous sample is illuminated by the X-ray free-electron laser (X-FEL) with a duration of $10^{-15}$ second and a repetition rate of 10 Hz.

In one embodiment, the compound is a chemical drug.

In one embodiment, the chemical drug is doxorubicin.

In one embodiment, during reconstructing the coherent diffraction image patterns with a computer, the method further comprises steps of: (d-1-1) rotating the coherent diffraction image patterns by 180 degrees; (d-1-2) shifting the coherent diffraction image patterns after rotation pixel-by-pixel to identify an origin; and (d-1-3) after identifying the origin, averaging each coherent diffraction image pattern before rotation and after rotation.

In one embodiment, after the step of averaging, the method further comprises a step of: (d-2) cropping the averaged coherent diffraction image patterns.

In one embodiment, after the step of cropping, the method further comprises steps of: (d-3-1) applying a Guided Hybrid Input-Output (GHIO) method to each coherent diffraction image pattern to obtain first preliminary reconstructions; (d-3-2) using a Fourier transformation to exclude a missing central speckle of each first preliminary reconstruction followed by a reverse Fourier transformation to fill up missing pixels of each first preliminary reconstruction, so as to obtain second preliminary reconstructions; (d-3-3) rotating the second preliminary reconstructions by 180 degrees and shifting the rotated second preliminary reconstructions 0.1 pixel-by-0.1 pixel to identify an origin; and (d-3-4) after identifying the origin, averaging each second preliminary reconstruction before rotation and after rotation.

In one embodiment, after the step of averaging each second preliminary reconstruction before rotation and after rotation, the method further comprises a step of: (d-4) performing a final reconstruction by combining the Guided Hybrid Input-Output (GHIO) method and a Shrink wrap algorithm (SW), so as to acquire the image of the lipid vesicle containing the compound.

To achieve the above objective, another embodiment of the invention discloses a method for examining a quality of a chemical drug contained by a liposome in water. The method comprises the following steps of: (a) providing an aqueous sample, wherein the aqueous sample comprises the liposome and ammonium sulphate (($NH_4$)$_2SO_4$); (b) illuminating the aqueous sample with an X-ray free-electron laser (X-FEL); (c) with an image sensor, collecting a plurality of coherent diffraction image patterns of the aqueous sample being illuminated; (d) reconstructing the coherent diffraction image patterns with a computer to obtain a reconstructed image; and (e) inspecting a conformation and size of the chemical drug in the reconstructed image so as to determine the quality of the chemical drug in the aqueous sample.

In one embodiment, wherein the concentration of the ammonium sulphate in the aqueous sample ranges from 1M to 6M.

In one embodiment, wherein the liposome has a size ranging from 70 nm to 250 nm.

In one embodiment, the concentration of the liposome in the aqueous sample ranges from 0.5 liposome/$\mu m^3$ to 1 liposome/$\mu m^3$.

In one embodiment, the X-ray free-electron laser (X-FEL) is 3.9613 keV photon pulses and the aqueous sample is illuminated by the X-ray free-electron laser (X-FEL) with a duration of $10^{-15}$ second and a repetition rate of 10 Hz.

In one embodiment, the chemical drug is doxorubicin.

Accordingly, this work utilized the X-ray free electron laser (X-FEL) to implement coherent diffraction imaging (CDI) of individual liposome particles in water, with or without inserted doxorubicin nanorods. In spite of the low cross section, the diffracted intensity of blank (drug-free) liposomes was sufficient for spatial reconstruction yielding quantitative structural information. When the particles contained doxorubicin, the structural parameters of the nanorods can be measured. In both cases, the information went well beyond what can be obtained by small-angle X-ray scattering (SAXS) and electron microscopy. This is important for the potential drug efficiency optimization and, in general, for X-FEL analysis of individual low-cross-section nanoparticles.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
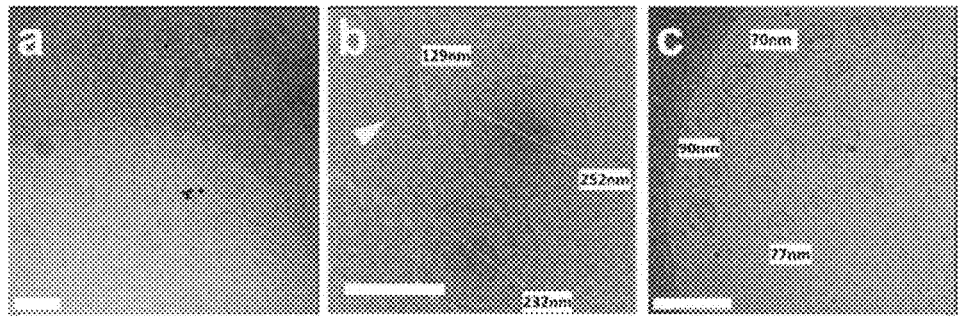
FIG. 1: Cryo-electron microscopy images of liposome particles. (a) blank and (b) doxorubicin-containing liposomes (the black dots in (a) are Au nanoparticles decorating one of the liposomes). (c) Processed doxorubicin-containing liposome compliant with the human therapy requirements, with more uniform size and shape. Scale bars=200 nm.

The embodiments of the invention will be apparent from the following detailed description, which proceeds with reference to the accompanying drawings, wherein the same references relate to the same elements. Specific structures and function details disclosed herein are only for the illustrative purpose for describing the exemplary embodiment of this disclosure. However, this disclosure can be specifically implemented through many replacements, and should not be explained as being restricted to only the embodiment disclosed herein. Moreover, all publications mentioned or cited in this disclosure are incorporated by reference to the same extent as if each individual publication or patent specification were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In the description of this disclosure, it is to be understood that the terms "center", "transversal", "up", "down", "left", "right", "vertical", "horizontal", "top", "bottom", "inside" and "outside" indicating the orientation or position relationships are the orientation or position relationships based on the drawing, are only provided for the purposes of describing this disclosure and simplifying the description, but do not indicate or imply that the directed devices or elements must have the specific orientations or be constructed and operated in the specific orientations, and thus cannot be understood as the restriction to this disclosure. In addition, the terms "first", and "second" are used for the illustrative purpose only and cannot be understood as indicating or implying the relative importance or implicitly specifying the number of indicated technical features. Therefore, the features restricted by "first" and "second" may expressly or implicitly comprise one or multiple ones of the features. In the description of this disclosure, unless otherwise described, the meaning of "multiple" comprises two or more than two. In addition, the terms "comprises" and any modification thereof intend to cover the non-exclusive inclusions.

In the description of this disclosure, it needs to be described that, unless otherwise expressly stated and limited, the terms "mount", "link" and/or "connect" should be construed broadly. For example, they may be referred to a fixed connection, detachable connection or connecting integrally, or they may be referred to a mechanical or an electrical connection; or, they may be referred to a direct connection or an indirect connection through an intermediate medium or an inter-communication between two elements. It will be apparent to those skilled in the art that the specific meanings of the above terms in this application may be understood according to the specific conditions.

The terms used herein are for the purpose of describing only specific embodiments and are not intended to limit the exemplary embodiments. Unless the contexts clearly indicate otherwise, the singular form "one", "a" and "an" used here further intend to include plural forms. It should also be understood that the terms "comprising" and/or "including" are used herein to describe the features to describe the presence of stated features, integers, steps, operations, units and/or elements without excluding the presence or addition of one or more other features, integers, steps, operations, units, elements, and/or combinations thereof.

Figure 6A:
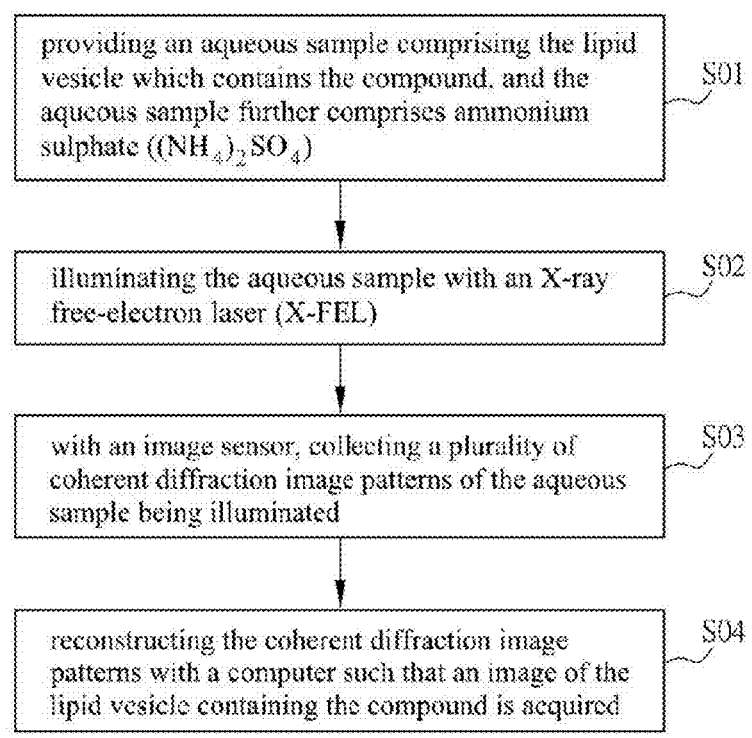
FIG. 6A is a flow chart of the method for imaging a compound contained by a lipid vesicle in water according to one embodiment of the invention.

Please refer to FIG. 6A, which is a flow chart of the method for imaging a compound contained by a lipid vesicle in water according to one embodiment of the invention. The method for imaging a compound contained by a lipid vesicle in water comprises the following Steps S01 to S04. The compound can be a chemical drug in nanoscale, which preferably doxorubicin. Step S01: providing an aqueous sample comprising the lipid vesicle which contains the compound, and the aqueous sample further comprises ammonium sulphate (($NH_4$)$_2$$SO_4$). Step S02: illuminating the aqueous sample with an X-ray free-electron laser (X-FEL). Step S03: with an image sensor, collecting a plurality of coherent diffraction image patterns of the aqueous sample being illuminated. Step S04: reconstructing the coherent diffraction image patterns with a computer such that an image of the lipid vesicle containing the compound is acquired.

In this method, the concentration of the ammonium sulphate in the aqueous sample ranges from 1M to 6M. The concentration of the ammonium sulphate in the aqueous sample can be 1.0M, 1.5M, 2.0M, 2.5M, 3.0M, 3.5M, 4.0M, 4.5M, 5.0M, 5.5M, 6.0M, or any rational number between 1M and 6M. The lipid vesicle can be a liposome or a micelle. When the lipid vesicle is a liposome, such liposome preferably has a size ranging from 70 nm to 250 nm, which can be 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, or any integral between 70 nm to 250 nm. Also, the concentration of the liposome in the aqueous sample may range from 0.5 liposome/$\mu m^3$ to 1 liposome/$\mu m^3$.

As shown in the following experimental examples, the X-ray free-electron laser (X-FEL) used in this method can be 3.9613 keV photon pulses, 425.4 μJ/pulse on an average, with a duration of $10^{-15}$ second and a repetition rate of 10 Hz.

Figure 6B:
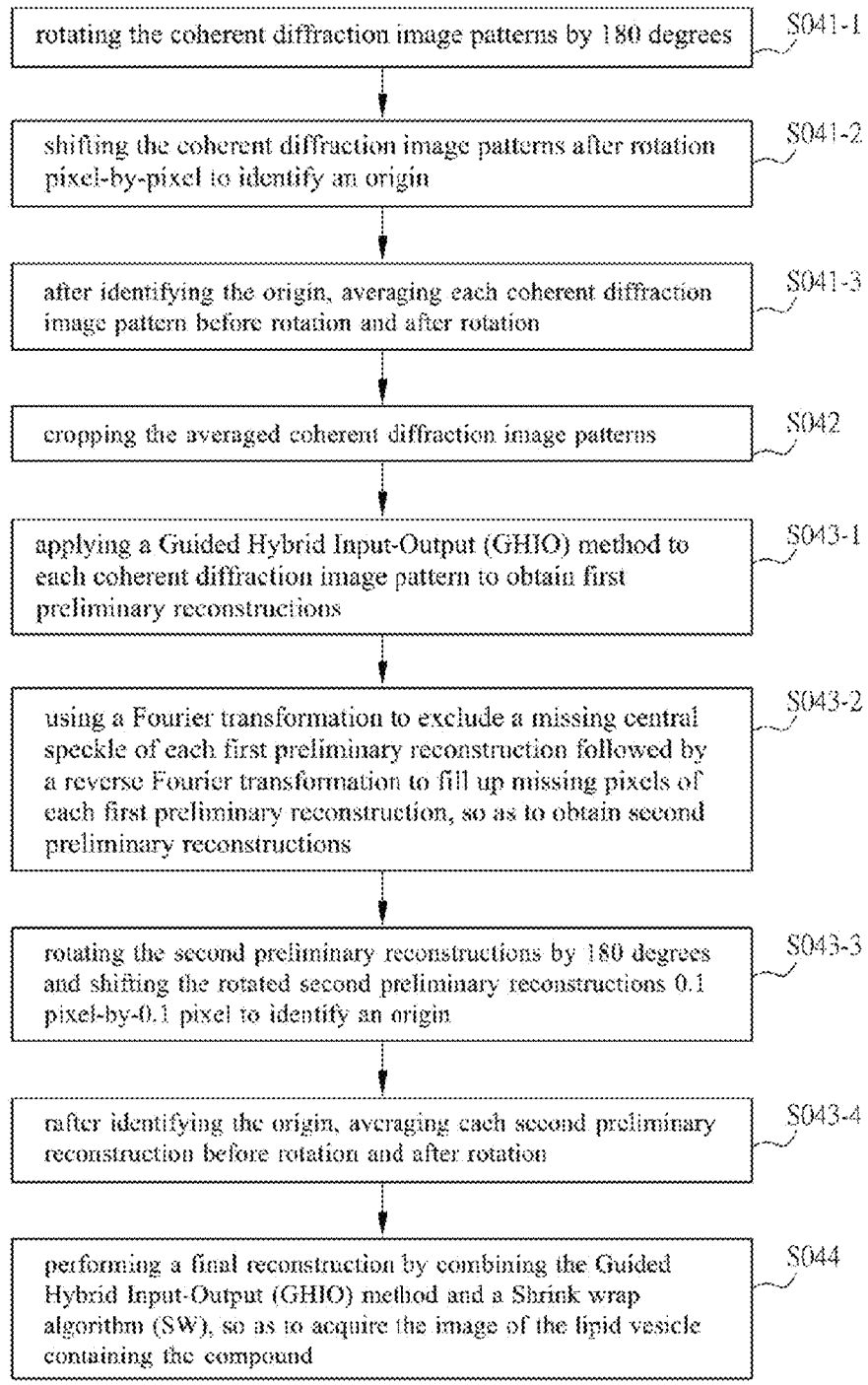
FIG. 6B is a flow chart of the method for imaging a compound contained by a lipid vesicle in water according to one embodiment of the invention.

Please refer to FIG. 6B, which is a flow chart representing a more detailed steps of reconstructing the coherent diffraction image patterns. In Step S04, reconstructing the coherent diffraction image patterns with the computer may further comprise the flowing steps. Step S041-1: rotating the coherent diffraction image patterns by 180 degrees. Step S041-2: shifting the coherent diffraction image patterns after rotation pixel-by-pixel to identify an origin. Step S041-3: after identifying the origin, averaging each coherent diffraction image pattern before rotation and after rotation. Step S042: cropping the averaged coherent diffraction image patterns. Step S043-1: applying a Guided Hybrid Input-Output (GHIO) method to each coherent diffraction image pattern to obtain first preliminary reconstructions. Step S043-2: using a Fourier transformation to exclude a missing central speckle of each first preliminary reconstruction followed by a reverse Fourier transformation to fill up missing pixels of each first preliminary reconstruction, so as to obtain second preliminary reconstructions. Step S043-3: rotating the second preliminary reconstructions by 180 degrees and shifting the rotated second preliminary reconstructions 0.1 pixel-by-0.1 pixel to identify an origin. Step S043-4: after identifying the origin, averaging each second preliminary reconstruction before rotation and after rotation. Step S044: performing a final reconstruction by combining the Guided Hybrid Input-Output (GHIO) method and a Shrink wrap algorithm (SW), so as to acquire the image of the lipid vesicle containing the compound. The details will be discussed in the following experimental examples.

Figure 7:
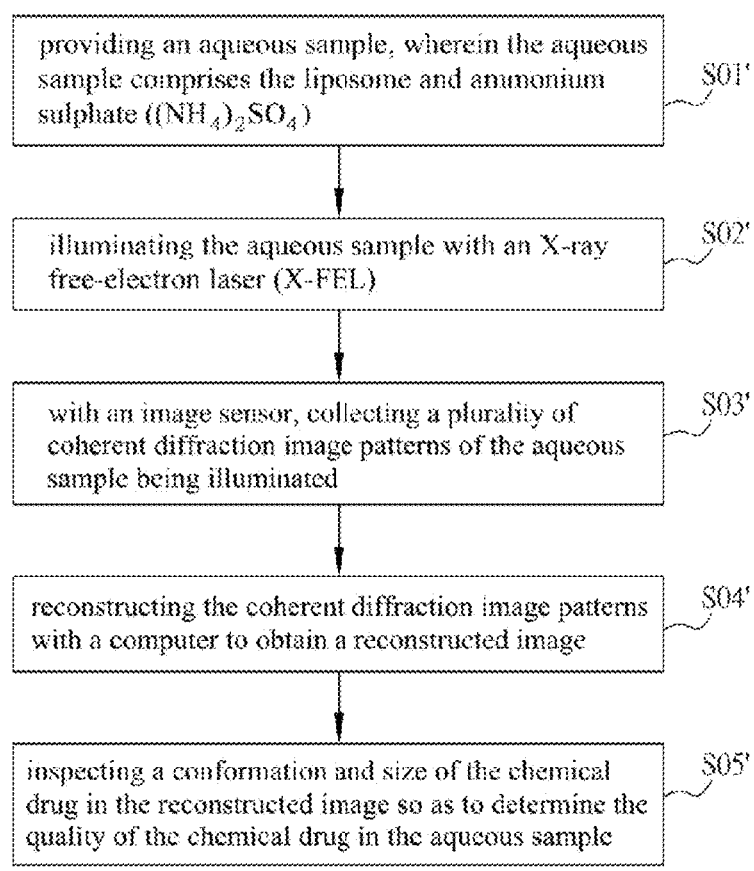
FIG. 7 is a flow chart of the method for examining a quality of a chemical drug contained by a liposome in water according to another embodiment of the invention.

Please refer to FIG. 7, which is a flow chart of the method for examining a quality of a chemical drug contained by a liposome in water according to another embodiment of the invention. The method for examining a quality of a chemical drug contained by a liposome in water primarily utilizes the imaging method provided by the preceding embodiment, and comprises the following Steps S01' to S05'. Step S01': providing an aqueous sample, wherein the aqueous sample comprises the liposome and ammonium sulphate (($NH_4$)$_2$$SO_4$). Step S02': illuminating the aqueous sample with an X-ray free-electron laser (X-FEL). Step S03': with an image sensor, collecting a plurality of coherent diffraction image patterns of the aqueous sample being illuminated. Step S04': reconstructing the coherent diffraction image patterns with a computer to obtain a reconstructed image. Step S05': inspecting a conformation and size of the chemical drug in the reconstructed image so as to determine the quality of the chemical drug in the aqueous sample.

Similarly, in this method, the concentration of the ammonium sulphate in the aqueous sample may ranges from 1M to 6M. The liposome may have a size ranging from 70 nm to 250 nm and the concentration of the liposome in the aqueous sample preferably ranges from 0.5 liposome/$\mu m^3$ to 1 liposome/$\mu m^3$. The X-ray free-electron laser (X-FEL) used here may also be 3.9613 keV photon pulses, with a duration of $10^{-15}$ second and a repetition rate of 10 Hz.

The other variations or connection relationship to other elements of each detail elements of the method can refer to the previous embodiments, and they are not repeated here.

To illustrate the functions and characteristics of the methods provided by the aforementioned embodiments, there are several experimental examples shown below.

Experimental Examples

Materials and Methods

The cryo-EM was performed with a JOEL 2100fx instrument equipped with a direct detection device (DDD) 5K×4K pixels camera and a cryogenic sample holder. The specimens were prepared with a Leica EM GP instrument that rapidly froze the liposome particles in vitreous ice.

CDI tests were performed at the SACLA X-FEL using 3.9613 keV photon pulses with 425.4 μJ/pulse on the average, 10 fs duration and 10 Hz repetition rate. The pulses were focused on the sample, down to 1.3×1 $\mu m^2$, using a Kirkpatrick-Baez (KB) mirror system.

The particle solution was placed in a micro-liquid enclosure array (MLEA) sample chip[4] with 24×24 enclosures, sealed by 100 nm thick SiN membranes on the two sides. Each enclosure had a volume of 20×20×2 µm³. The MLEA was placed in the vacuum system of the SACLA Multiple Application X-ray Imaging Chamber (MAXIC) instrument.[33]

The chip position was scanned with respect to the X-ray beam so that each enclosure was hit by only one X-FEL pulse per scan. If the enclosure contained a particle, this created a diffraction pattern before being destroyed.

The solution had a concentration corresponding to about 1 liposome per 1 µm³. This minimized the probability of probing more than one liposome per pulse, which would otherwise adversely affect the CDI reconstruction.[34,35] Note, however, that the concentration could not be too low, to avoid a large percentage of null diffraction results. We found that the above concentration was optimal, producing >50% useable diffraction patterns corresponding >100 successful reconstructions from each MLEA chip.

The diffraction patterns were recorded with a MPCCD (multiport charge-coupled device) octal sensor with a total area of 2399×2399 pixels (pixel size=50×50 µm²).[36] The sample-detector distance was 1.51 m.

The CDI data analysis and reconstruction procedure was the following. First, since the diffraction pattern must be center-symmetric, we rotated the acquired pattern by 180 degrees and shifted the image pixel-by-pixel to find the origin by minimizing the L1 norm. After identifying the origin, we averaged the original pattern and the rotated one. Second, we cropped 471×471 and 601×601 pixels for the analyzed patterns. The corresponding estimated pixel resolutions of the reconstructed images were 20.0 nm and 15.7 nm.

Third, for each pattern the GHIO method[16] was applied to obtain a preliminary reconstruction. We then Fourier transformed these reconstructions excluding the missing central speckle, and used the reverse transform to fill up missing pixels. Finally, we repeated the first step but limited the image shifting to 0.1 pixels, obtaining a refined pattern. For each refined pattern, a final reconstruction by combining GHIO and the Shrink wrap algorithm (SW) was performed. A loose support was used to guarantee that no relevant signal was removed when applying the support constraint. For each iteration of the reconstruction, 16 initial random phases were generated to obtain 16 different reconstructed images. To generate a new support for the next iteration, the average of the 16 images was Gaussian-smoothed and a background was subtracted. Instead of finding a convergent support as in the conventional SW method, we forced the new support to be smaller (by <10 pixels) than the previous one.

The evolution of the 16 reconstructed images was monitored over 20 iterations. The support changed from loose to over-cropped; the distribution of the 16 reconstructed images was accordingly modified from divergent to convergent, and then back to divergent. The final support was obtained when most reconstructed images were consistent. The GHIO reconstruction was then reiterated based on the final pattern and the final support. The reconstruction was terminated when the error metric stagnated.

Results and Discussion

FIG. 1 shows cryo-EM images of blank and doxorubicin containing liposomes. Note that the therapeutical use is only effective and officially approved for rod-shaped drug particles inside liposomes within a narrow size range. FIGS. 1(b) and 1(c) reveal significant deviations from this standard: the liposome size ranges from about 80 nm to >250 nm (and requires size filtering in the industrial drug production process). Furthermore, whereas some liposomes contain doxorubicin with the correct shape (i.e., rods—see for example the arrow-marked particle in FIG. 1(b)), others contain doxorubicin with unacceptable shapes. Furthermore, some liposomes contain no doxorubicin at all, and others are enclosed in larger liposomes. These characteristics cannot be detected by particle-averaging techniques such as SAXS—whereas they are crucial to therapy, its optimization and the mandatory controls of industrial manufacturing for human use.

Figure 2:
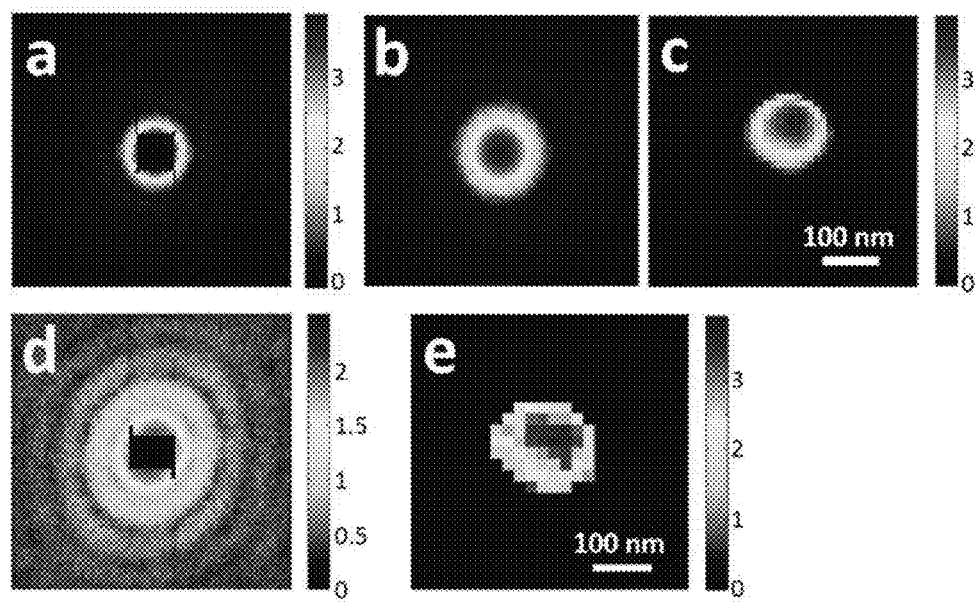
FIG. 2: Representative CDI patterns for individual liposomes with no doxorubicin. (a)-(c) shows typical results for one liposome: (a) diffraction pattern; (b) the same pattern after GHIO processing (initial reconstruction); (c) the corresponding reconstructed image in real space (the error factor is 0.1741). Scale bars=100 nm. (d) and (e) diffraction pattern and reconstructed image of another drug-free liposome. The color scales are in arbitrary unit.

FIG. 2 shows representatives CDI results for two individual liposomes with no doxorubicin; FIG. 2(a) is a diffraction pattern, FIG. 2(b) is the pattern after processing with the Guided Hybrid Input-Output (GHIO)[15] method and FIG. 2(c) is the resulting reconstruction. In this widely used image processing technique, a circular constraint improves the appearance of the images but it does not in any way alters the essential geometric features. FIGS. 2(d) and 2(e) show the diffraction pattern and the reconstruction for another individual liposome. From the reconstructions, this work directly extracted the size of each liposome, about 100±20 nm in both cases.

Concerning spatial resolution, for CDI it is limited by the largest detectable scattering vector, i.e., by the largest angle at which diffraction can be measured. The present experimental setup can potentially achieve 10 nm resolution with optimized conditions. However, from a small-angle-x-ray-scattering (SAXS-like) we estimate that the real resolution is about 20 nm. This, of course, is not the ultimate performance: with improved signal-to-noise levels better resolutions are feasible. Note that our time resolution (see below) was 10 fs, making factors like rotational or diffusion motions irrelevant. Other factors like aggregation of nanoparticles are ruled out by the reconstructed images, in agreement with the results from cryo-EM.

Figure 5:
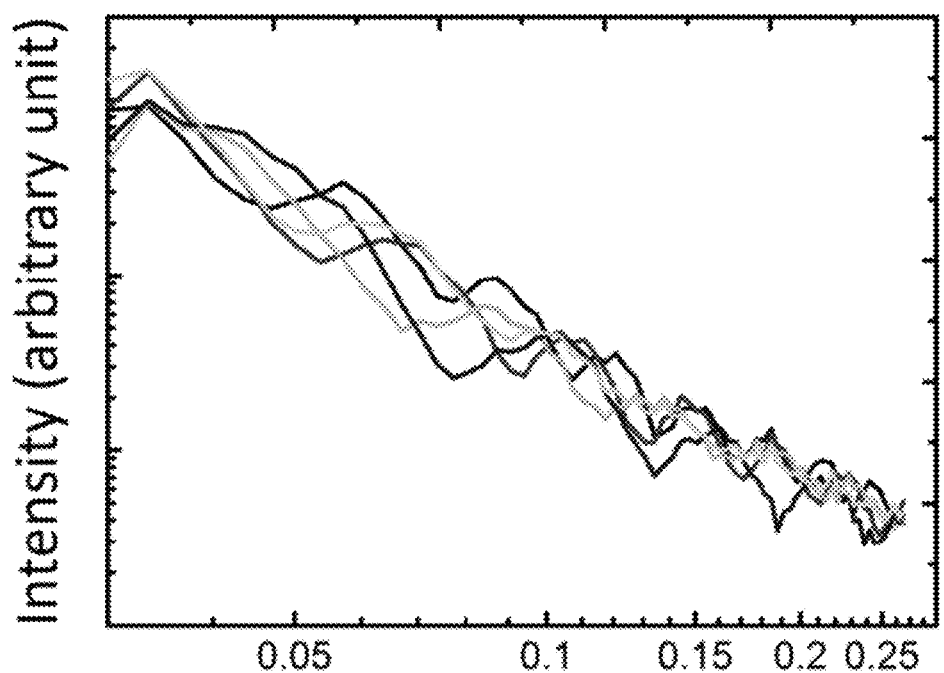
FIG. 5: SAXS-like curves derived from our CDI patterns. As explained in the text, each curve corresponding to an individual liposome. The sizes so obtained are in the 100-200 nm range.

To corroborate the CDI-derived particle sizes, we calculated SAXS-like curves from the diffraction patterns, by integrating over all directions the intensity for each q-value (q=momentum transfer magnitude). FIG. 5 shows the curves so obtained for five different particles. The connection with real SAXS curves is only approximate, since our CDI patterns do not average over different particles. However, fits of the SAXS like curves with a standard procedure[32] reasonably corroborated the sizes extracted CDI by giving results in the 100-200 nm range.

Figure 3:
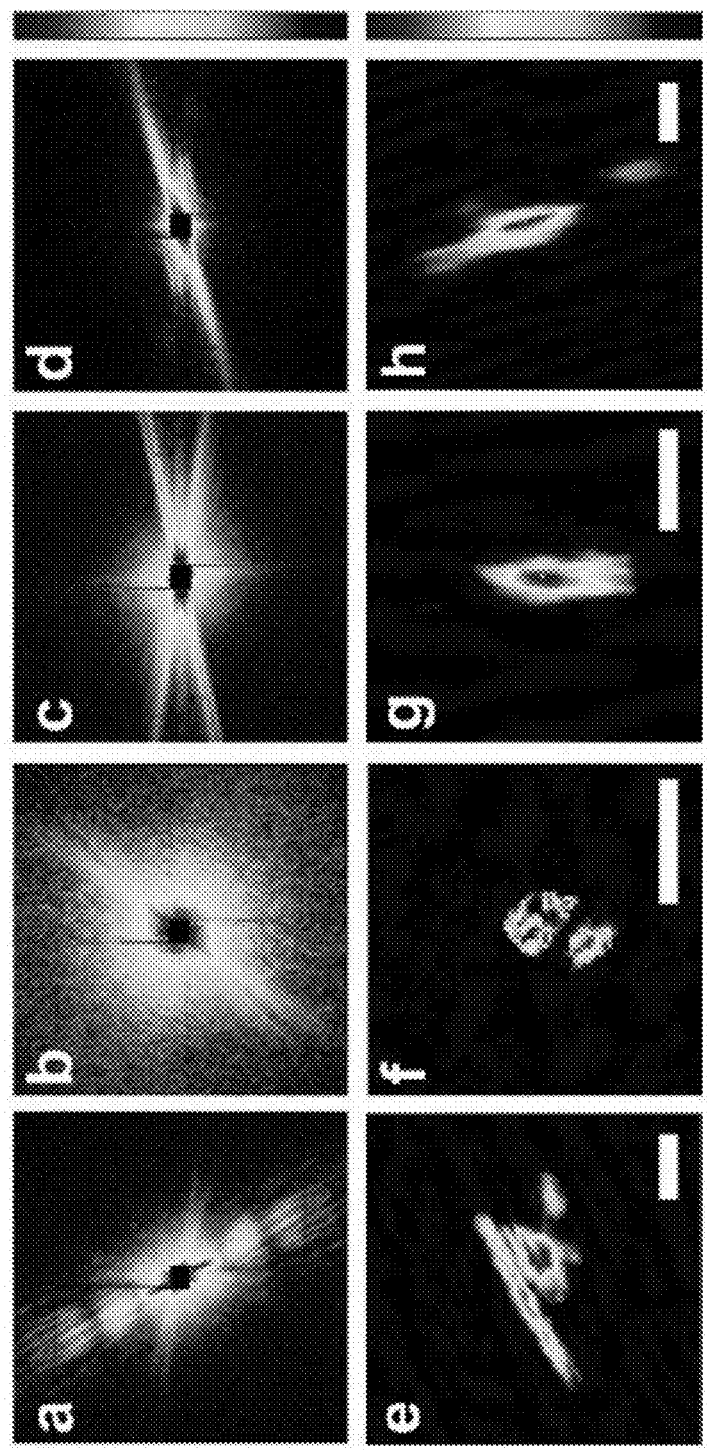
FIG. 3: CDI patterns of four individual doxorubicin-containing liposomes. (a)-(d), diffraction patterns; (e)-(h), their corresponding reconstructed images. Bars=200 nm.

The results of FIG. 2 raise an intriguing question: how can CDI patterns be detected at all if the nominal scattering power of the constituents is weak? The answer can be provided by the practical composition of our liposomes. Indeed, they were produced with the same industrial process used for drug containing liposomes. As a result, they are likely to include significant amounts of residual ammonium sulphate, $(NH_4)_2SO_4$, from the precursor solution. We estimated that the diffracted intensity by this compound in 2M solution, much lower than the saturation concentration (about 6M) which has an electron density 30-50% higher than water, can produce the contrast levels detected in our liposome patterns. FIG. 3 shows CDI results for four doxorubicin-containing liposomes in liquid environment. The reconstructions clearly reveal rod-shaped doxorubicin particles. The lengths and widths seen in the reconstructions correspond of course to the two-dimensional projections of the rods. The projection values are in the range 40-80 nm (width) and 120-200 nm (length), and the aspect ratio is 0.25-0.6. Such results are quite reasonable in light of the cryo-EM data.

Figure 4:
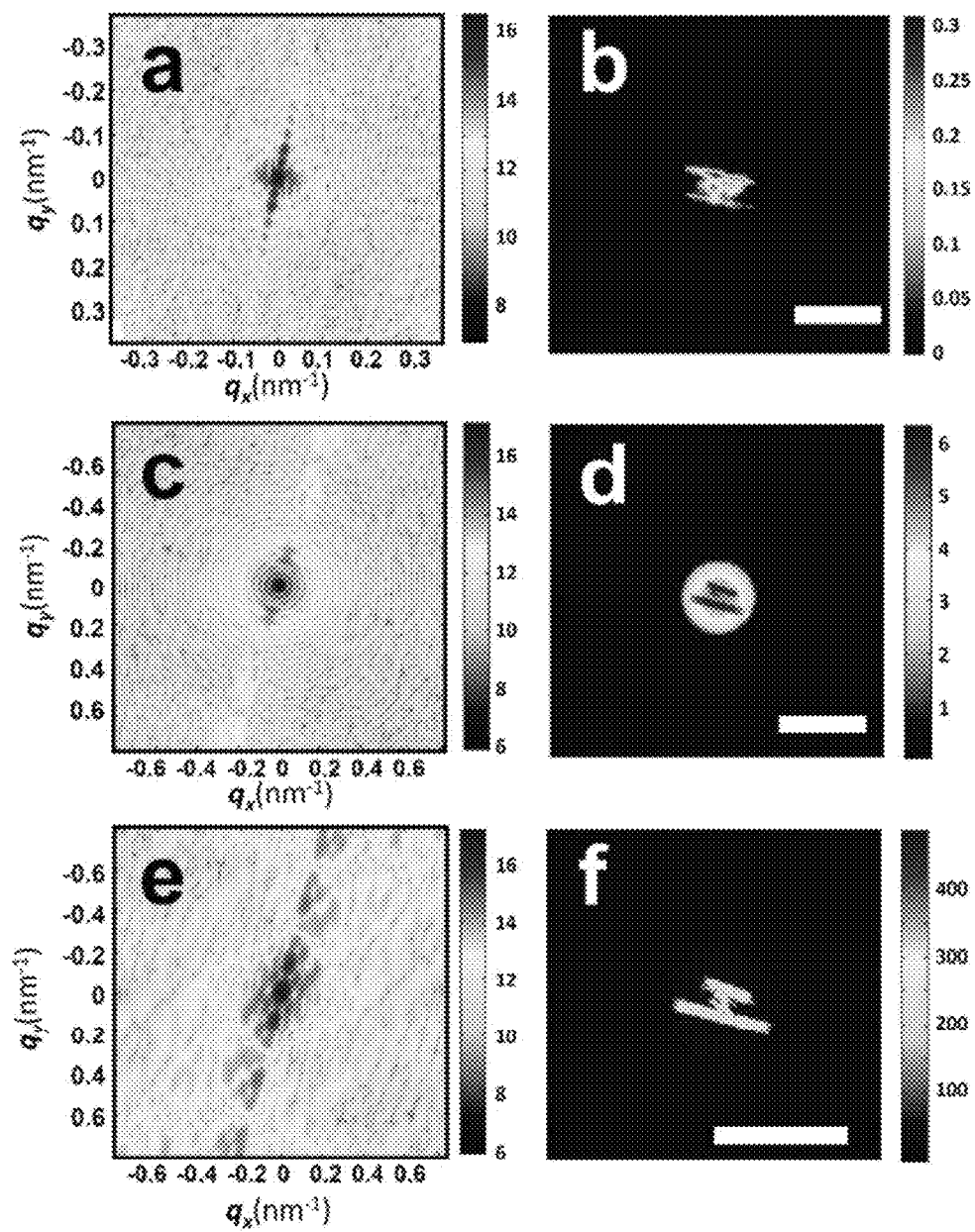
FIG. 4: Simulated CDI patterns of individual doxorubicin-containing liposomes and their corresponding reconstructed images. (a) and (b) are the diffraction pattern and the CDI reconstructed result experimentally obtained for a drug containing liposome. (c) and (d) are results for a solution containing 2M of ($NH_4$)$_2SO_4$, as used in the production process. These simulations show that the liposome-related features should be visible, whereas in FIG. 4 they are not. (e) and (f) are results for a ($NH_4$)$_2SO_4$ solution concentration reduced to 500 mM: the liposome-related features disappeared. Scale bars=200 nm.

Note that the diffraction patterns of FIG. 3 show only rod-related features but no circular ones, as expected for the liposomes. To explain this point, we must consider again the role of $(NH_4)_2SO_4$, from the precursor solution. FIG. 4 shows the results of simulation. Specifically, FIG. 4(c) shows a simulated diffraction pattern for a drug-containing liposome, modified from FIG. 4(a) by including a simulated circular diffraction pattern caused by the $(NH_4)_2SO_4$ (2M concentration) in the liposome. FIG. 4(d) shows the corresponding reconstruction, revealing the spherical liposome, which is not visible in the real reconstructions of FIG. 4(b). FIGS. 4(e) and 4(f) show the simulated pattern and the reconstruction for a system similar to that of FIGS. 4(c) and 4(d), but in a water solution with a sulphate concentration reduced to 500 mM. it has no longer see features related to the liposome.

For example, the data of this work show that the concentration of $(NH_4)_2SO_4$ in blank liposome is about 2M, whereas with drug rods the concentration reduced to <1M. The measurements, including those for blank liposomes, provide therefore important chemical information on the solution, specifically on the ammonium sulphate concentration in the liquid within individual drug-containing liposomes, difficult to obtain by other means. The measured reduction of ammonium sulphate concentration substantiates the incorporation of the sulphate in the rods during their formation and the subsequent depletion from the solution as previously hypothesized.

Conclusions

The performances of the SACLA X-FEL were sufficient to extend the technique of individual nanoparticle imaging by CDI reconstruction from highly x-ray absorbing systems to weak absorbers. The results on blank liposomes were quantitatively consistent with those of cryo-EM. Furthermore, X-FEL CDI detected doxorubicin nanorods enclosed in liposomes and measured their structural properties.

The results of this work are important in view of the optimization of the industrial drug loading in liposome nanoparticles as required for official certification for human use. In more general terms, they demonstrate that X-FEL CDI can now image individual nanoparticles with nominally low diffraction cross sections, in a liquid environment and with <100 nm size—and therefore it has a significantly broader scope than suggested by previous tests.

The present results are thus important by themselves, in particular since liposome nanocarriers are the most widely used ones at present and we can envision the future to other systems such as Au nanocarriers, even more so since the case of liposomes is particularly difficult with respect to other cases.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

REFERENCES

1. D. Pile, *Nature Photon.*, 2011, 5, 456-457.
2. P. Emma, R. Akre, J. Arthur, R. Bionta, C. Bostedt, J. Bozek, A. Brachmann, P. Bucksbaum, R. Coffee and F.-J. Decker, *Nature Photon.*, 2010, 4, 641-647.
3. T. Ishikawa, H. Aoyagi, T. Asaka, Y. Asano, N. Azumi, T. Bizen, H. Ego, K. Fukami, T. Fukui and Y. Furukawa, *Nature Photon.*, 2012, 6, 540-544.
4. T. Kimura, Y. Joti, A. Shibuya, C. Song, S. Kim, K. Tono, M. Yabashi, M. Tamakoshi, T. Moriya and T. Oshima, *Nat. Commun.*, 2014, 5, 3052.
5. M. Gallagher-Jones, Y. Bessho, S. Kim, J. Park, S. Kim, D. Nam, C. Kim, Y. Kim, O. Miyashita and F. Tama, *Nat. Commun.*, 2014, 5, 3798.
6. G. van der Schot, M. Svenda, F. R. Maia, M. Hantke, D. P. DePonte, M. M. Seibert, A. Aquila, J. Schulz, R. Kirian and M. Liang, *Nat. Commun.*, 2015, 6, 5704.
7. T. Ekeberg, M. Svenda, C. Abergel, F. R. Maia, V. Seltzer, J.-M. Claverie, M. Hantke, O. Jonsson, C. Nettelblad and G. van der Schot, *Phys. Rev. Lett.*, 2015, 114, 098102.
8. M. Watari, R. McKendry, M. Voegtli, G. Aeppli, Y. Soh, X. Shi, G. Xiong, X. Huang, R. Harder, I. K. Robinson, *Nat. Mater.* 2011, 10, 862-866.
9. D. Nam, J. Park, M. Gallagher-Jones, S. Kim, S. Kim, Y. Kohmura, H. Naitow, N. Kunishima, T. Yoshida, T. Ishikawa T and C. Song, *Phys. Rev. Lett.*, 2013, 110, 098103.
10. D. Papahadjopoulos, T. Allen, A. Gabizon, E. Mayhew, K. Matthay, S. Huang, K. Lee, M. Woodle, D. Lasic and C. Redemann, *Proc. Natl. Acad. Sci. USA*, 1991, 88, 11460-11464.
11. A. Gabizon, R. Catane, B. Uziely, B. Kaufman, T. Safra, R. Cohen, F. Martin, A. Huang and Y. Barenholz, *Cancer Res.*, 1994, 54, 987-992.
12. D. W. Northfelt, F. J. Martin, P. Working, P. A. Volberding, J. Russell, M. Newman, M. A. Amantea and L. D. Kaplan, *J. Clin. Pharmacol.*, 1996, 36, 55-63.
13. J. R. Fienup, *Appl. Opt.*, 1982, 21, 2758-2769.
14. V. Elser, *J. Opt. Soc. Am.*, 2003, 20, 40-55.
15. H. H. Bauschke, P. L. Combettes and D. R. Luke, *J. Opt. Soc. Am.*, 2002, 19, 1334-1345.
16. C. Chen, J. Miao, C. Wang and T. Lee, *Phys. Rev. B*, 2007, 76, 064113.
17. T. M. Allen and P. R. Cullis, *Science*, 2004, 303, 1818-1822.
18. A. Samad, Y. Sultana and M. Aqil, *Curr. Drug. Deliv.*, 2007, 4, 297-305.
19. B. C. Keller, *Trends Food Sci. Tech.*, 2001, 12, 25-31.
20. F. Arcamone, G. Cassinelli, G. Fantini, A. Grein, P. Orezzi, C. Pol and C. Spalla, *Biotechnol. Bioeng.*, 1969, 11, 1101-1110.
21. R. I. Pakunlu, Y. Wang, M. Saad, J. J. Khandare, V. Starovoytov and T. Minko, *J. Control. Release*, 2006, 114, 153-162.
22. T. Kubo, T. Sugita, S. Shimose, Y. Nitta, Y. Ikuta and T. Murakami, *Int. J. Oncol.*, 2000, 17, 309-324.
23. A. A. Gabizon, *Cancer Invest.*, 2001, 19, 424-436.
24. B. Uziely, S. Jeffers, R. Isacson, K. Kutsch, D. Wei-Tsao, Z. Yehoshua, E. Libson, F. M. Muggia and A. Gabizon, *J. Clin. Oncol.*, 1995, 13, 1777-1785.
25. S. A. Abraham, D. N. Waterhouse, L. D. Mayer, P. R. Cullis, T. D. Madden and M. B. Bally, *Methods Enzymol*, 2005, 391, 71-97.
26. S. K. Hobbs, W. L. Monsky, F. Yuan, W. G. Roberts, L. Griffith, V. P. Torchilin and R. K. Jain, *Proc. Natl. Acad. Sci. USA*, 1998, 95, 4607-4612.
27. Y.-M. Wu, C.-H. Wang, J.-w. Chang, Y.-y. Chen, N. Miyazaki, K. Murata, K. Nagayama and W.-H. Chang, *J. Phys. D*, 2013, 46, 494008.
28. Y.-M. Wu, J.-W. Chang, C.-H. Wang, K. Nagayama, N. Miyazaki, K. Murata and W.-H. Chang, *Microsc. Microanal.*, 2015, 21, 2145-2146.
29. M. Almgren, K. Edwards and G. Karlsson, *Colloids Surf. A*, 2000, 174, 3-21.

30 I. V. Zhigaltsev, N. Maurer, Q.-F. Akhong, R. Leone, E. Leng, J. Wang, S. C. Semple and P. R. Cullis, *J. Control. Release*, 2005, 104, 103-111.
31 N. Weiner, F. Martin and M. Riaz, *Drug. Dev. Ind. Pharm.*, 1989, 15, 1523-1554.
32 M. Kotlarchyk and S. H. Chen, *J. Chem. Phys.*, 1983, 79, 2461-2469.
33 C. Song, K. Tono, J. Park, T. Ebisu, S. Kim, H. Shimada, S. Kim, M. Gallagher-Jones, D. Nam, T. Sato, T. Togashi, K. Ogawa, Y. Joti, T. Kameshima, S. Ono, T. Hatsui, S. Iwata, M. Yabashi and T. Ishikawa, *J. Appl. Cryst.*, 2014, 47, 188-197.
34 Y. Takahashi, A. Suzuki, N. Zettsu, T. Oroguchi, Y. Takayama, Y. Sekiguchi, A. Kobayashi, M. Yamamoto and M. Nakasako, *Nano Lett*, 2013, 13, 6028-6032.
35 M. J. Bogan, D. Starodub, C. Y. Hampton and R. G. Sierra, *J. Phys. B*, 2010, 43, 194013.
36 M. Yabashi, T. Ishikawa, in XFEL/SPring-8 Beamline Technical Design Report ver. 2.0. 42-46 (Experimental facility group, SPring-8 joint project for XFEL, Hyogo, 2010).

What is claimed is:

1. A method for imaging an individual nanoparticle which is a compound contained by a lipid vesicle in water, comprising:
   providing an aqueous sample comprising the lipid vesicle which contains the compound;
   illuminating the aqueous sample with an X-ray free-electron laser (X-FEL);
   with an image sensor, collecting a plurality of coherent diffraction image patterns of the aqueous sample being illuminated; and
   reconstructing the coherent diffraction image patterns with a computer such that a reconstructed image of the individual nanoparticle which is the lipid vesicle containing the compound is acquired;
   wherein during reconstructing the coherent diffraction image patterns with a computer, the method further comprises steps of:
   rotating the coherent diffraction image patterns by 180 degrees;
   shifting the coherent diffraction image patterns after rotation pixel-by-pixel to identify an origin; and
   after identifying the origin, averaging each coherent diffraction image pattern before rotation and after rotation.

2. The method according to claim 1, wherein the aqueous sample further comprises ammonium sulphate (($NH_4)_2SO_4$), and the concentration of the ammonium sulphate in the aqueous sample ranges from 1 M to 6 M.

3. The method according to claim 1, wherein the lipid vesicle is a liposome or a micelle.

4. The method according to claim 3, wherein the liposome has a size ranging from 70 nm to 250 nm.

5. The method according to claim 3, wherein the concentration of the liposome in the aqueous sample ranges from 0.5 liposome/$\mu m^3$ to 1 liposome/$\mu m^3$.

6. The method according to claim 1, wherein the X-ray free-electron laser (X-FEL) is 3.9613 keV photon pulses.

7. The method according to claim 6, wherein the X-ray free-electron laser (X-FEL) is 425.4 µJ/pulse on an average.

8. The method according to claim 7, wherein the aqueous sample is illuminated by the X-ray free-electron laser (X-FEL) with a duration of $10^{-15}$ second and a repetition rate of 10 Hz.

9. The method according to claim 1, wherein the compound is a chemical drug.

10. The method according to claim 9, wherein the chemical drug is doxorubicin.

11. The method according to claim 1, wherein after the step of averaging, the method further comprises a step of:
    cropping the averaged coherent diffraction image patterns.

12. The method according to claim 11, wherein after the step of cropping, the method further comprises steps of:
    applying a Guided Hybrid Input-Output (GHIO) method to each coherent diffraction image pattern to obtain first preliminary reconstructions;
    using a Fourier transformation to exclude a missing central speckle of each first preliminary reconstruction followed by a reverse Fourier transformation to fill up missing pixels of each first preliminary reconstruction, so as to obtain second preliminary reconstructions;
    rotating the second preliminary reconstructions by 180 degrees and shifting the rotated second preliminary reconstructions 0.1 pixel-by-0.1 pixel to identify an origin; and
    after identifying the origin, averaging each second preliminary reconstruction before rotation and after rotation.

13. The method according to claim 12, wherein after the step of averaging each second preliminary reconstruction before rotation and after rotation, the method further comprises a step of:
    performing a final reconstruction by combining the Guided Hybrid Input-Output (GHIO) method and a Shrink wrap algorithm (SW), so as to acquire the image of the lipid vesicle containing the compound.

14. A method for examining a quality of an individual nanoparticle which is a chemical drug contained by a liposome in water, comprising:
    providing an aqueous sample, wherein the aqueous sample comprises the liposome, the liposome contained the chemical drug;
    illuminating the aqueous sample with an X-ray free-electron laser (X-FEL);
    with an image sensor, collecting a plurality of coherent diffraction image patterns of the aqueous sample being illuminated;
    reconstructing the coherent diffraction image patterns with a computer to obtain a reconstructed image of the individual nanoparticle which is the liposome contained the chemical drug; and
    inspecting a conformation and size of the chemical drug in the reconstructed image so as to determine the quality of the chemical drug in the aqueous sample;
    wherein during reconstructing the coherent diffraction image patterns with a computer, the method further comprises steps of:
    rotating the coherent diffraction image patterns by 180 degrees;
    shifting the coherent diffraction image patterns after rotation pixel-by-pixel to identify an origin; and
    after identifying the origin, averaging each coherent diffraction image pattern before rotation and after rotation.

15. The method according to claim 14, wherein the aqueous sample further comprises ammonium sulphate (($NH_4)_2SO_4$), and the concentration of the ammonium sulphate in the aqueous sample ranges from 1 M to 6 M.

16. The method according to claim 14, wherein the liposome has a size ranging from 70 nm to 250 nm.

17. The method according to claim 14, wherein the concentration of the liposome in the aqueous sample ranges from 0.5 liposome/$\mu m^3$ to 1 liposome/$\mu m^3$.

18. The method according to claim 14, wherein the X-ray free-electron laser (X-FEL) is 3.9613 keV photon pulses and the aqueous sample is illuminated by the X-ray free-electron laser (X-FEL) with a duration of $10^{-15}$ second and a repetition rate of 10 Hz.

19. The method according to claim 14, wherein the chemical drug is doxorubicin.

* * * * *